United States Patent
Geistert

(10) Patent No.: US 7,493,173 B2
(45) Date of Patent: Feb. 17, 2009

(54) ELECTRODE LINE

(75) Inventor: Wolfgang Geistert, Rheinfelden (DE)

(73) Assignee: Biotronik CRM Patent AG (CH)

( * ) Notice: Subject to any disclaimer, the term of this patent is extended or adjusted under 35 U.S.C. 154(b) by 319 days.

(21) Appl. No.: 11/128,892

(22) Filed: May 13, 2005

(65) Prior Publication Data

US 2005/0256558 A1    Nov. 17, 2005

(30) Foreign Application Priority Data

May 14, 2004    (DE)  ................ 10 2004 025 101
Jul. 9, 2004    (DE)  ................ 10 2004 034 336

(51) Int. Cl.
*A61N 1/05*    (2006.01)
*A61B 5/04*    (2006.01)

(52) U.S. Cl. .................. 607/119; 607/122; 600/374

(58) Field of Classification Search .......... 600/372, 600/373, 374, 377, 381; 606/129; 607/115, 607/116, 119, 122, 123, 125

See application file for complete search history.

(56) References Cited

U.S. PATENT DOCUMENTS

| | | | |
|---|---|---|---|
| 4,103,690 A * | 8/1978 | Harris ................ | 607/128 |
| 5,549,109 A | 8/1996 | Samson et al. | |
| 5,683,445 A | 11/1997 | Swoyer | |
| 5,755,766 A * | 5/1998 | Chastain et al. ......... | 607/122 |
| 5,800,495 A | 9/1998 | Machek et al. | |
| 5,803,928 A * | 9/1998 | Tockman et al. ......... | 607/122 |
| 5,968,085 A * | 10/1999 | Morris et al. .............. | 607/116 |
| 6,363,287 B1 * | 3/2002 | Brabec et al. ............... | 607/120 |
| 6,408,213 B1 | 6/2002 | Bartig et al. | |
| 6,512,957 B1 * | 1/2003 | Witte ..................... | 607/116 |
| 6,529,779 B1 | 3/2003 | Sutton | |
| 6,567,704 B2 * | 5/2003 | Sundquist et al. .......... | 607/119 |
| 2002/0147412 A1 * | 10/2002 | Reinke et al. .............. | 600/547 |
| 2003/0109914 A1 | 6/2003 | Westlund et al. | |
| 2003/0171796 A1 | 9/2003 | Hine et al. | |
| 2003/0195602 A1 * | 10/2003 | Boling ..................... | 607/122 |
| 2003/0216771 A1 | 11/2003 | Osypka et al. | |
| 2003/0220676 A1 | 11/2003 | Helland | |
| 2005/0070986 A1 * | 3/2005 | Tockman et al. ........... | 607/122 |

* cited by examiner

*Primary Examiner*—Carl H. Layno
*Assistant Examiner*—Jon-Eric C. Morales
(74) *Attorney, Agent, or Firm*—Hahn Loeser & Parks LLP

(57) ABSTRACT

An electrode line for intraluminal or intracardiac use for connection to a cardiac pacemaker, comprises an elongate, flexurally soft electrode line body having a distal end at which or in the proximity of which is arranged at least one distal electrode which is electrically connected to the electrical connecter and has an electrically conducting outside surface. The electrode line has a lumen for receiving a guide wire or the like. The distal electrode and the distal opening of the lumen in the region of the distal end of the electrode line body are arranged in mutually laterally displaced relationship with respect to a longitudinal direction of the electrode line body so that a guide wire issuing from the distal opening is guided in laterally displaced relationship past the distal electrode and the distal opening is arranged without longitudinal displacement beside a proximal end of the distal electrode or is arranged with a longitudinal displacement in displaced relationship distally with respect to the proximal end of the distal electrode.

20 Claims, 3 Drawing Sheets

18

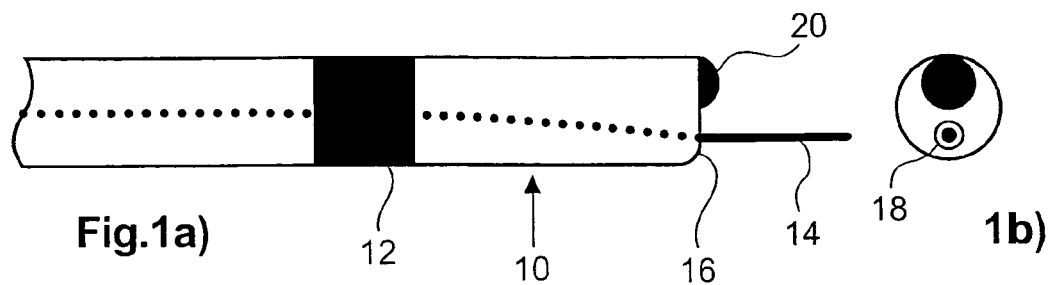
Fig.1a) 1b)
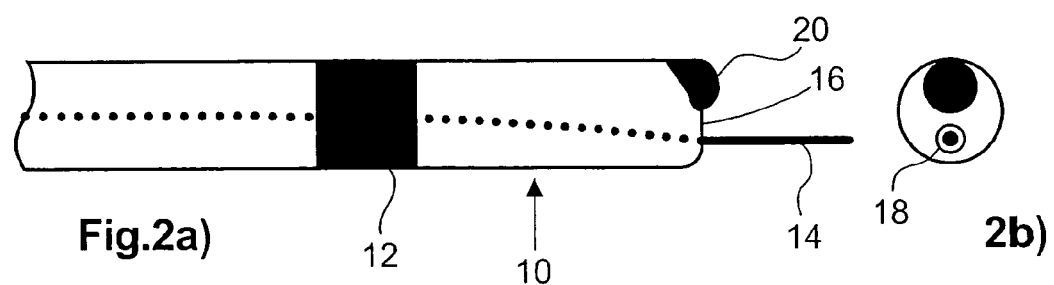
Fig.2a) 2b)
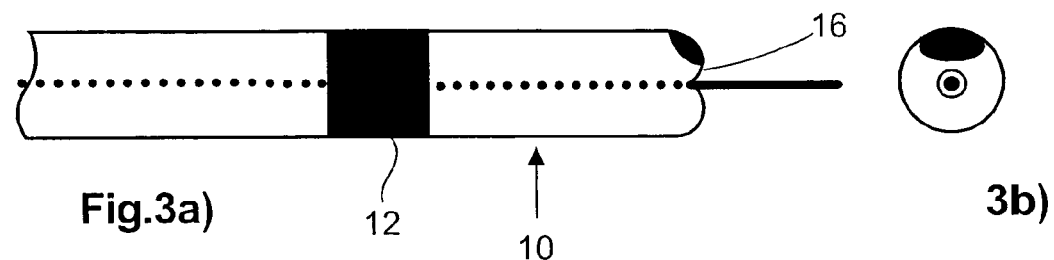
Fig.3a) 3b)
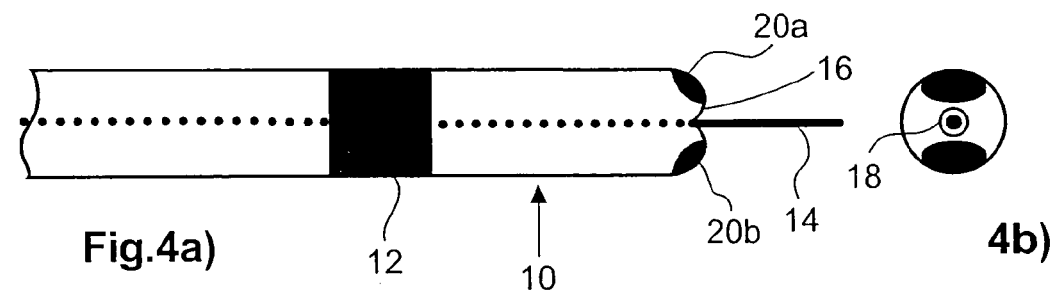
Fig.4a) 4b)
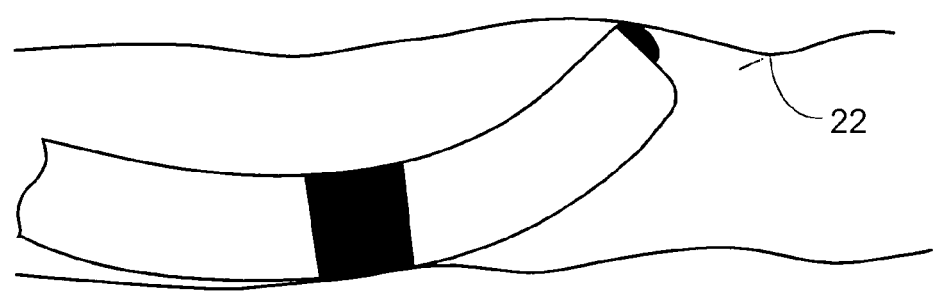
Fig.5)

ELECTRODE LINE

BACKGROUND OF THE INVENTION

The invention concerns an electrode line for intraluminal or intracardiac use which is suitable for connection to an electrostimulation device such as a cardiac pacemaker, defibrillator, cardioverter or the like. The electrode line has an elongate, flexurally soft electrode line body having a proximal end, at which is arranged an electrical connecting means for making an electrical connection to a stimulation device. The electrode line body also has a distal end, at which or in the proximity of which is arranged at least one distal electrode which is electrically connected to the electrical connecting means and has an electrically conducting outside surface. Provided in the electrode line body is a lumen for accommodating a guide wire. That lumen extends from a distal opening in the region of the distal end of the electrode line body to a proximal opening which is arranged proximally of the distal opening, preferably in the region of the proximal end of the electrode body. The distal opening is of such a configuration and arrangement that a guide wire can issue from the lumen through the distal opening.

Electrode lines of that kind are already known from the state of the art, for example from U.S. Pat. No. 5,800,495. Described therein is an electrode line having a lumen and a distal opening which is suitable for receiving a stiletto.

Taking that art as the basic starting point, the invention seeks to provide an electrode line which offers the physician further areas of use.

BRIEF SUMMARY OF THE INVENTION

According to the invention, that aim is achieved by an electrode line of the kind set forth in the opening part of this specification, wherein the distal electrode of the electrode line and the distal opening which allows the guide wire to issue in the region of the distal end of the electrode line are arranged in mutually laterally displaced relationship with respect to the longitudinal direction of the electrode line body. That lateral displacement makes it possible to achieve reliable, constant wall contact for the distal electrode when the electrode line is introduced into a blood vessel by way of a guide wire. So that, with an arrangement of that kind for the distal electrode, which is laterally displaced with respect to the distal opening, hooking of the distal end of the electrode line body during insertion of the electrode line along a guide wire is prevented. It is further provided that the distal opening is arranged at least beside a proximal end of the distal electrode or in front of same—that is to say, closer to the distal end of the electrode line body than the proximal end of the distal electrode.

The electrode line body is preferably pre-bent at least in the region of its distal end in such a way that it curves in the direction of the laterally arranged distal electrode. That ensures good constant wall contact for the laterally arranged electrode. The electrode line body assumes its curvature at least after removal of a guide wire, that is to say the electrode line body can be so designed that its pre-curvature configuration is eliminated by an inserted guide wire or a stiletto.

The pre-curvature configuration preferably extends at least in a plane defined by the longitudinal direction of the electrode line body as well as the distal opening and the distal electrode, in the direction of the distal electrode.

In a particularly preferred variant of the invention, the distal opening is disposed in a distal front end of the electrode line body and is arranged not centrally but in laterally displaced relationship with respect to a center line of the electrode line body.

In addition, preferably provided on the electrode line body beside the distal electrode is at least one second electrode which is preferably in the form of a ring electrode, which is arranged proximally of the distal electrode and is disposed at a longitudinal spacing relative thereto and surrounds the lumen in the interior of the electrode line body. That preferred variant permits bipolar stimulation or bipolar sensing of cardiac potentials (bipolar sensing). Instead of a single distal electrode it is also possible to provide two distal electrodes which are each respectively arranged in laterally displaced relationship with respect to the distal opening of the lumen. In particular in the last-mentioned variant, the distal opening of the lumen is preferably disposed in a distal end face of the electrode line body and in that case, can also be arranged centrally as the two distal electrodes can be arranged in laterally displaced relationship at both sides of the distal opening.

An alternative, also preferred variant of the electrode line with a distal opening at a longitudinal spacing relative to a proximal end of the distal electrode is, in its longitudinal portion which is disposed distally of the distal opening, of a smaller diameter than the electrode line body in its longitudinal portion which is in proximally adjoining relationship with the distal opening. With this variant, the distal opening is arranged in a shark mouth-like configuration beside the distal opening, the distal electrode extending proximally beyond the distal opening.

A preferred variant consists of a system with an electrode line of the above-described kind and a guide wire. In that case, the guide wire is electrically insulated outwardly along the major part of its length and has an electrode surface at its distal end or in the proximity thereof, which is electrically connected to a proximal end of the guide wire and which is in the form of a stimulation and/or sensing electrode. The idea here is that, instead of a "normal" guide wire, a very substantially insulated guide wire is used in conjunction with the electrode line described herein. In the case of such a guide wire, only a small portion at or in the proximity of the distal end and a small portion at or in the proximity of the proximal end is not insulated. The small portion in the proximity of the distal end can be used as an active electrode in order to record cardiac potentials at the potential positioning location of the electrode or to simulate the heart. The small portion in the proximity of the proximal end then serves as a connecting location for a cable to a detection and/or stimulation device. The two non-insulated portions are electrically connected together. The whole serves to sound out the optimum placement location for the electrode.

An alternative variant consists of a system with an electrode line of the above-described kind as a first electrode line, into the lumen of which is inserted a second, thinner electrode line which is longitudinally displaceable relative to the first electrode line. The second electrode line carries at least one ring or tip electrode at the distal end thereof or in the proximity thereof. The ring or tip electrode is in the form of a stimulation and/or sensing electrode and is electrically connected to a proximal end of the second electrode line. The second electrode line differs from the above-described guide wire in that its ring or tip electrode is electrically connected to an electrode line plug at the proximal end of the second electrode line, which makes it possible for the second electrode line to be connected to an electrically active medical device, in particular to an implant such as a cardiac pacemaker, defibrillator or the like.

The very thin, second electrode line makes it possible to reach positions which are "deeper" in the branched vessel system. Multi-polar electrode systems can be implemented in that way. For example, stimulation can be effected or cardiac potentials can be taken off between one pole (tip or ring electrode) of the very thin, second electrode line and one pole (electrode) of the first electrode line.

In an advantageous embodiment of all (first) electrode lines described herein, a seal is disposed in the proximity of the exit opening for the guide wire or the second electrode line, the seal preventing blood from penetrating into the guide wire lumen or the electrode line.

BRIEF DESCRIPTION OF THE SEVERAL VIEWS OF THE DRAWINGS

The invention will now be described in greater detail by means of embodiments by way of example with reference to the drawings in which:

FIG. 1 shows a variant in which the distal opening is arranged beside the proximal end of a distal electrode, FIG. 2 shows a variant similar to FIG. 1, in which the distal electrode also extends proximally of the distal opening, FIG. 3 shows a variant with a central distal opening and laterally arranged distal electrode, FIG. 4 shows a variant similar to FIG. 3, with two laterally arranged distal electrodes, FIG. 5 shows a variant similar to FIG. 1, with an electrode line body which is pre-curved at least in the region of the illustrated distal end.

DETAILED DESCRIPTION OF THE INVENTION

Figure 6:
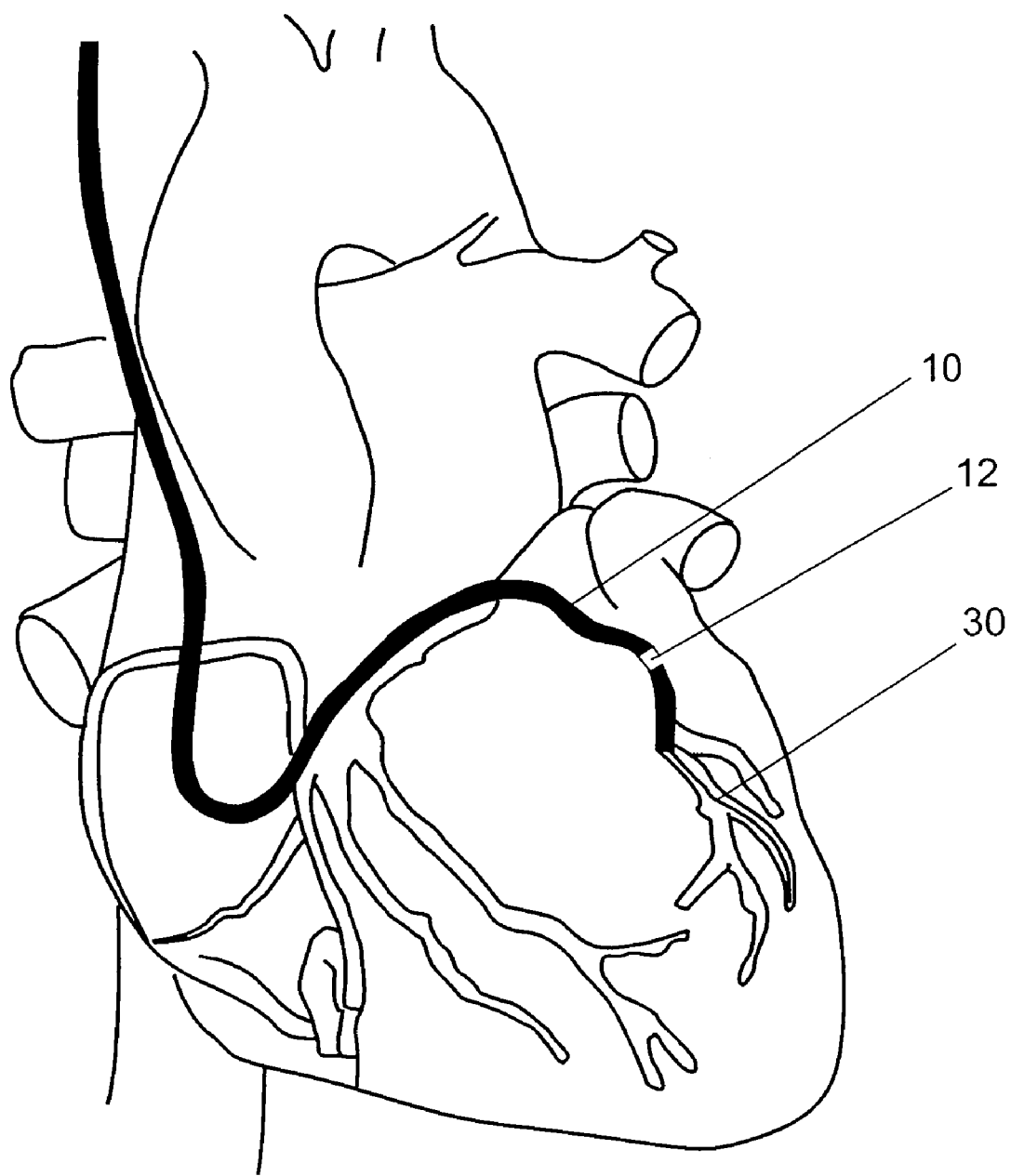
FIG. 6 shows a system comprising a first electrode line corresponding to FIGS. 1 through 5 and a thinner second electrode line introduced into the lumen of the first electrode line.

FIGS. 1 through 5 each show the distal end of an electrode line 10. That electrode line 10 has the usual features (not shown) of an electrode line, namely a proximal end with an electrical connecting means for connection of the electrode line to an electrostimulation device, for example an implantable cardiac pacemaker or an implantable cardioverter/defibrillator. The electrode line body of the electrode 10, whose distal end portion is shown in FIGS. 1 through 4, is usually formed by a helically wound conductor which imparts the desired flexural softness and strength to the electrode line and moreover, electrically connects at least one electrode, for example a ring electrode 12, to the electrical connecting means at the proximal end of the electrode line. The helical coil (not shown in the Figures) is usually surrounded on the outside by an elastic sleeve, for example of silicone. In the interior, the helical coil encloses a lumen which serves to guide a guide wire 14 which is shown for the sake of better description in FIGS. 1 through 4 although it is not part of the invention.

The lumen which extends in the interior of the electrode line body and which is not shown in detail herein but which is indicated by the guide wire illustrated in broken line, terminates in the region of a distal end 16 of the electrode line 10 in a distal opening 18. The guide wire 14 can issue from the lumen within the electrode line body through the distal opening 18.

A respective distal electrode 20 is also of significance in the context which is relevant here. There are two distal electrodes, 20a and 20b, in FIG. 4.

FIGS. 1 through 4 each show a side view of the distal end of the electrode line 10 (FIGS. 1a through 4a) and a view onto the distal front end of a respective electrode line 10 (FIGS. 1b through 4b).

It can be seen from all Figures that the respective distal electrode 20 or the distal electrodes 20a and 20b are arranged in laterally displaced relationship with respect to the respective distal opening 18. The lateral displacement relates to the longitudinal direction of the electrode line 10 and is to be particularly clearly seen in the end views in FIGS. 1b through 4b. As in particular the end views in FIGS. 1b through 4b show, the distal electrodes 20 or 20a, 20b respectively are each arranged beside the respective distal opening 18. The distal electrodes 20 and 20a, 20b respectively thus advantageously do not have any opening themselves, through which the guide wire has to pass.

In that way, the ring electrodes 12 and the distal electrodes (tip electrodes) 20 and 20a, 20b respectively can be of a configuration like conventional ring and tip electrodes and for example in a preferred embodiment are coated fractally by means of iridium or titanium nitrite or iridium oxide.

FIG. 5 shows an electrode line corresponding to FIG. 1, the distal end portion of which is pre-bent in such a way that the electrode line body curves after removal of the guide wire. That makes it possible to achieve secure constant wall contact in respect of the laterally arranged distal electrode 20, as can be seen from FIG. 5, when the relative position of the distal electrode 20 in relation to the vessel wall 22, which is indicated here for the sake of illustration is considered.

Preferably, the curvature is such that not just the distal electrode 20 but also the proximal electrode 12 are pressed against the vessel wall.

Pre-shaped electrode lines which curve by virtue of their prestressing after removal of a guide wire or a stiletto are basically known. The pre-shaping can be achieved inter alia by a suitably shaped helical coil on the electrode line body or by a suitable external plastic sleeve. Particular significance is attributed in each case to the pre-shaping however, in conjunction with the variants illustrated herein which have a laterally arranged distal electrode.

FIG. 6 is a diagrammatic view of an electrode line 10, into the lumen of which is inserted a second thinner electrode line 30. As can be seen from FIG. 6, the second electrode line 30 issues from the first electrode line 10 at its distal end and from there projects into further, more finely branched blood vessels of a heart shown in FIG. 6. The first electrode line 10 is introduced through the right atrium of the heart into the coronary sinus and from there in a lateral vein branching from the coronary sinus in which finally the distal electrode 20 and possibly the proximal electrode 12 are positioned. The second electrode line 30 also carries a tip electrode (not visible in FIG. 6) at its distal end 31.

Figure 7:
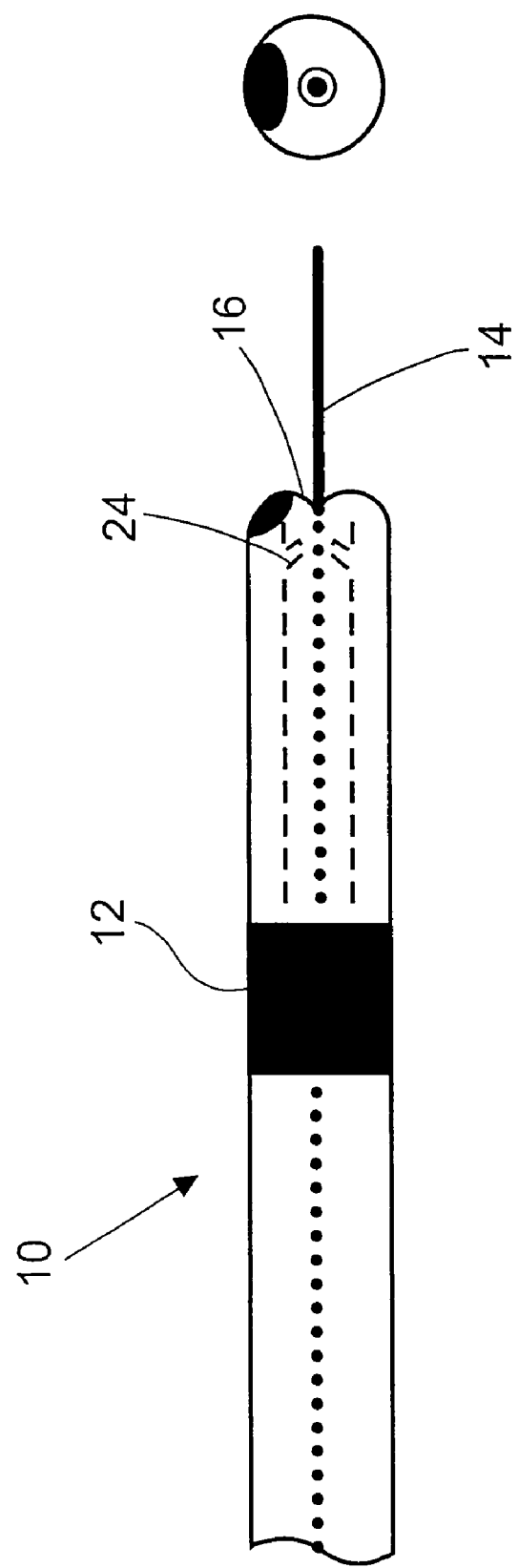
FIG. 7 shows a diagrammatic sectional view of the distal end of an electrode line corresponding to FIGS. 1 through 5 to show a lip seal in the proximity of the distal end of the lumen.

Finally, FIG. 7 is a diagrammatic view showing the distal end of a first electrode line 10, similar to FIG. 3. This view diagrammatically shows how a lip seal 24 is arranged in the lumen of the electrode line 10 in the proximity of the distal end 16, wherein the guide wire 14 can issue through the lip seal 24. That lip seal 24 prevents blood from penetrating into the lumen of the electrode line 10, more specifically both in the situation where a guide wire 14 passes through the lip seal 24, as shown in FIG. 7, and also in the situation in which no guide wire 14 is inserted into the lumen of the electrode line 10. In the latter case the lips of the lip seal are in contact with each other and close the distal end of the lumen of the electrode line 10.

What is claimed is:

1. An electrode line for intraluminal or intracardiac use for connection to an electrostimulation device such as a cardiac pacemaker, defibrillator, cardioverter or the like, comprising:
an elongate, flexurally soft electrode line body having a proximal end, at which an electrical connecting means for making an electrical connection to an electrostimulation device is arranged,
and a distal end, at which or in the proximity of which is arranged at least one distal electrode which is electrically connected to the electrical connecting means and has an electrically conducting outside surface,
and in which there is provided a lumen for receiving a guide wire or the like, which extends from a proximal opening in the region of the proximal end of the electrode line body to a distal opening in the region of the distal end of the electrode line body, wherein the distal opening is of such a configuration and arrangement that a guide wire can issue from the lumen through the distal opening,
wherein the at least one distal electrode and the distal opening in the region of the distal end of the electrode line body are arranged in mutually laterally displaced relationship with respect to a cross-sectional orientation of the electrode line body so that a guide wire issuing from the distal opening is guided in laterally displaced relationship past the distal electrode, and the distal opening is arranged without cross-sectional displacement beside a proximal end of the distal electrode or is arranged with a cross-sectional displacement in displaced relationship distally with respect to the proximal end of the distal electrode,
wherein the distal electrode faces substantially in a direction forward of the distal end.

2. An electrode line as set forth in claim 1, wherein a proximal electrode is arranged proximally of the distal electrode at a spacing relative to the distal end of the electrode line body.

3. An electrode line as set forth in claim 2, wherein the proximal electrode is a ring electrode which surrounds the lumen.

4. An electrode line as set forth in claim 2, additionally comprising a guide wire, wherein along the major part of its length, the guide wire has an outwardly disposed electrical insulation and an electrode surface at its distal end or in the proximity thereof, which is electrically connected to a proximal end of the guide wire and is in the form of a stimulation and/or sensing electrode.

5. An electrode line as set forth in claim 3, additionally comprising a second electrode line, which is adapted to be inserted into the lumen and which is longitudinally displaceable relative to the first electrode line and which has at least one ring or tip electrode at the distal end of the second electrode line or in the proximity thereof, wherein the ring or tip electrode is in the form of a stimulation and/or sensing electrode and is electrically connected to a proximal end of the second electrode line.

6. An electrode line as set forth in claim 5, additionally comprising a seal in the region of a distal end of the lumen, wherein the seal is adapted to permit a guide wire or the like to pass therethrough and to seal off the lumen in relation to a penetration of blood thereinto.

7. An electrode line as set forth in claim 6, wherein the seal is in the form of a lip seal.

8. An electrode line as set forth in claim 1, additionally comprising a guide wire, wherein along the major part of its length, the guide wire has an outwardly disposed electrical insulation and an electrode surface at its distal end or in the proximity thereof, which is electrically connected to a proximal end of the guide wire and is in the form of a stimulation and/or sensing electrode.

9. An electrode line as set forth in claim 1, additionally comprising a second electrode line, which is adapted to be inserted into the lumen and which is longitudinally displaceable relative to the first electrode line and which has at least one ring or tip electrode at the distal end of the second electrode line or in the proximity thereof, wherein the ring or tip electrode is in the form of a stimulation and/or sensing electrode and is electrically connected to a proximal end of the second electrode line.

10. An electrode line for intraluminal or intracardiac use for connection to an electrostimulation device such as a cardiac pacemaker, defibrillator, cardioverter or the like, comprising:
an elongate, flexurally soft electrode line body having a proximal end, at which an electrical connecting means for making an electrical connection to an electrostimulation device is arranged,
and a distal end, at which or in the proximity of which is arranged at least one distal electrode which is electrically connected to the electrical connecting means and has an electrically conducting outside surface,
and in which there is provided a lumen for receiving a guide wire or the like, which extends from a proximal opening in the region of the proximal end of the electrode line body to a distal opening in the region of the distal end of the electrode line body, wherein the distal opening is of such a configuration and arrangement that a guide wire can issue from the lumen through the distal opening,
wherein the at least one distal electrode and the distal opening in the region of the distal end of the electrode line body are arranged in mutually laterally displaced relationship with respect to a cross-sectional orientation of the electrode line body so that a guide wire issuing from the distal opening is guided in laterally displaced relationship past the distal electrode, and the distal opening is arranged without cross-sectional displacement beside a proximal end of the distal electrode or is arranged with a cross-sectional displacement in displaced relationship distally with respect to the proximal end of the distal electrode,
wherein the at least one distal electrode is in the form of a tip electrode that is biased relative to a center axis of the electrode line and is arranged at the distal end of the electrode line body,
wherein at least one of the distal electrode and the distal opening is asymmetrically radially displaced from the central axis of the electrode line.

11. An electrode line as set forth in claim 10, wherein the electrode line body is pre-bent at least in the region of its distal end in such a way that at least after removal of a guide wire, the electrode line body curves in the direction of the distal electrode at least in a plane defined by the cross-section of the electrode line body, as well as the distal opening and the distal electrode.

12. An electrode line as set forth in claim 10, wherein two distal electrodes are arranged laterally of the distal opening at the distal end of the electrode line body.

13. An electrode line as set forth in claim 12, wherein the distal opening is arranged centrally between the two distal electrodes.

14. An electrode line as set forth in claim 10, wherein the distal opening is arranged in displaced relationship with respect to a proximal end of the distal electrode in the distal direction.

15. An electrode line as set forth in claim 14, wherein in a proximal longitudinal portion disposed proximally of the distal opening the electrode line body is of a larger outside diameter than the distal electrode in its distal longitudinal portion disposed distally of the distal opening between the distal opening and the distal end of the electrode line body.

16. An electrode line as set forth in claim 10, wherein the distal opening is arranged with respect to the longitudinal direction of the electrode line body without a longitudinal spacing relative to the proximal end of the distal electrode.

17. An electrode line as set forth in claim 16, wherein a proximal electrode is arranged proximally of the distal electrode at a spacing relative to the distal end of the electrode line body.

18. An electrode line as set forth in claim 17, wherein the proximal electrode is a ring electrode which surrounds the lumen.

19. An electrode line for intraluminal or intracardiac use for connection to an electrostimulation device such as a cardiac pacemaker, defibrillator, cardioverter or the like, comprising:

an elongate, flexurally soft electrode line body having a proximal end, at which an electrical connecting means for making an electrical connection to a electrostimulation device is arranged, and a distal end, at which or in the proximity of which is arranged at least one distal electrode which is electrically connected to the electrical connecting means and has an electrically conducting outside surface, and in which there is provided a lumen for receiving a guide wire or the like, which extends from a proximal opening in the region of the proximal end of the electrode line body to a distal opening in the region of the distal end of the electrode line body, wherein the distal opening is of such a configuration and arrangement that a guide wire can issue from the lumen through the distal opening, wherein the at least one distal electrode and the distal opening in the region of the distal end of the electrode line body are arranged in mutually laterally displaced relationship with respect to a cross-sectional orientation of the electrode line body so that a guide wire issuing from the distal opening is guided in laterally displaced relationship past the distal electrode, and the distal opening is arranged without cross-sectional displacement beside a proximal end of the distal electrode or is arranged with a cross-sectional displacement in displaced relationship distally with respect to the proximal end of the distal electrode, additionally comprising a seal in the region of a distal end of the lumen, wherein the seal is adapted to permit a guide wire or the like to pass therethrough and to seal off the lumen in relation to a penetration of blood thereinto, and wherein the distal electrode and distal opening are disposed in a common cross-sectional plane extending radially from the central axis.

20. An electrode line as set forth in claim 19, wherein the seal is in the form of a lip seal.

\* \* \* \* \*